(12) United States Patent
Ramalhinho et al.

(10) Patent No.: US 12,350,098 B2
(45) Date of Patent: Jul. 8, 2025

(54) ULTRASOUND REGISTRATION

(71) Applicant: UCL Business Ltd, London (GB)

(72) Inventors: Joao Ramalhinho, London (GB); Matthew J. Clarkson, London (GB)

(73) Assignee: UCL BUSINESS LTD, London (GB)

( * ) Notice: Subject to any disclaimer, the term of this patent is extended or adjusted under 35 U.S.C. 154(b) by 532 days.

(21) Appl. No.: 17/630,024

(22) PCT Filed: Jul. 23, 2020

(86) PCT No.: PCT/GB2020/051770
§ 371 (c)(1),
(2) Date: Jan. 25, 2022

(87) PCT Pub. No.: WO2021/019217
PCT Pub. Date: Feb. 4, 2021

(65) Prior Publication Data
US 2022/0249056 A1 Aug. 11, 2022

(30) Foreign Application Priority Data

Jul. 26, 2019 (GB) ...................................... 1910756

(51) Int. Cl.
*A61B 8/00* (2006.01)
*G06T 7/11* (2017.01)
(Continued)

(52) U.S. Cl.
CPC ............ *A61B 8/4245* (2013.01); *A61B 8/463* (2013.01); *G06T 7/11* (2017.01); *G06T 7/248* (2017.01);
(Continued)

(58) Field of Classification Search
CPC ......... A61B 8/4245; A61B 8/463; G06T 7/11; G06T 7/248; G06T 7/337; G06T 7/74;
(Continued)

(56) References Cited

U.S. PATENT DOCUMENTS

2014/0193053 A1* 7/2014 Kadoury ................ A61B 90/36
382/128
2015/0279031 A1* 10/2015 Cavusoglu .............. G06T 7/277
382/103
(Continued)

FOREIGN PATENT DOCUMENTS

WO 2017200519 A1 11/2017

OTHER PUBLICATIONS

Wein, W., Brunke, S., Khamene, A., Callstrom, M. R., & Navab, N. (2008). Automatic CT-ultrasound registration for diagnostic imaging and image-guided intervention. Medical image analysis, 12(5), 577-585 (Year: 2008).*

(Continued)

*Primary Examiner* — Ping Y Hsieh
*Assistant Examiner* — Vaisali Rao Koppolu
(74) *Attorney, Agent, or Firm* — Grossman, Tucker, Perreault & Pfleger, PLLC; Donald J. Perreault (57) ABSTRACT

A computer implemented method is disclosed for identifying a pose of a probe by registering an ultrasound image with volumetric scan data. The volumetric scan data is processed (31) to determine simulated ultrasound images corresponding with a plurality of different poses of the probe. A feature vector is extracted (32) from each of the simulated ultrasound images and from the ultrasound image. The feature vector from the ultrasound image is compared (33) with each feature vector of the simulated ultrasound images to determine a distance or similarity for each simulated ultrasound image. At least one candidate image is selected (34), the at least one candidate image comprising a subset of the simulated ultrasound images that best matches the ultrasound image, based on the distance or similarity. The pose of the probe is identified (35) from the at least one candidate image.

20 Claims, 8 Drawing Sheets (51) Int. Cl.
  *G06T 7/246* (2017.01)
  *G06T 7/33* (2017.01)
  *G06T 7/73* (2017.01)

(52) U.S. Cl.
  CPC ............... *G06T 7/337* (2017.01); *G06T 7/74* (2017.01); *G06T 2207/10016* (2013.01); *G06T 2207/10132* (2013.01); *G06T 2207/20076* (2013.01); *G06T 2207/20081* (2013.01); *G06T 2207/20084* (2013.01); *G06T 2207/30101* (2013.01); *G06T 2207/30241* (2013.01); *G06T 2207/30244* (2013.01)

(58) Field of Classification Search
  CPC . G06T 2207/10016; G06T 2207/10132; G06T 2207/20076; G06T 2207/20081; G06T 2207/20084; G06T 2207/30101; G06T 2207/30241; G06T 2207/30244; G06T 2207/10072; G06T 7/30
  See application file for complete search history.

(56) References Cited

U.S. PATENT DOCUMENTS

| | | | |
|---|---|---|---|
| 2016/0113630 A1* | 4/2016 | Chang | G06T 7/30 600/440 |
| 2016/0113632 A1* | 4/2016 | Ribes | A61B 8/469 600/440 |
| 2017/0079623 A1* | 3/2017 | Kruecker | A61B 8/5261 |
| 2018/0270474 A1* | 9/2018 | Liu | A61B 6/5247 |
| 2020/0273184 A1* | 8/2020 | Dufour | A61B 8/4254 |
| 2021/0059762 A1* | 3/2021 | Ng | G06T 7/344 |

OTHER PUBLICATIONS

International Search Report and Written Opinion from corresponding PCT Appln. No. PCT/GB2020/051770, mailed Oct. 22, 2020.

Ramalhinho, Joao et al., "Registration of Untracked 2D Laparoscopic Ultrasound Liver Images to CT Using Content-Based Retrieval and Kinematic Priors", Oct. 8, 2019, 12th European Conference on Computer Vision, ECCV 2012, Springer Berlin Heidelberg, Berlin Germany, pp. 11-19.

Smistad, Erik et al., "Vessel Detection in Ultrasound Images Using Deep Convolutional Neural Networks", Sep. 27, 2016, Big Data Analytics in the Social and Ubiquitous Context: 5th International Workshop on Modeling Social Media, MSM 2014, 5th International Workshop on Mining Ubiquitous and Social Environments, Muse 2014 and First International Workshop on Machine, pp. 30-38.

Wein, W. et al., "Automatic CT-Ultrasound Registration for Diagnostic Imaging and Image-Guided Intervention", Medical Image Analysis, Oxford University Press, Oxford, GB, vol. 12, No. 5, Oct. 2008, pp. 577-585.

Search Report under Section 17(5) of United Kingdom Application No. GB1910756.4, dated Dec. 20, 2019, 4 pages.

* cited by examiner

ULTRASOUND REGISTRATION

FIELD OF THE INVENTION

The invention relates to registration of ultrasound scan data with volumetric scan data. More specifically, the invention relates to registration of laparoscopic ultrasound scan data with CT or MRI scan data.

BACKGROUND

Ultrasound information in combination with computed tomography (CT) may be advantageous in a number of clinical contexts. For example, a lesion in a patient's liver or kidney may be identified with by CT or MRI, and further characterisation of the lesion may be performed using ultrasound (US) imaging. Further examples are in performing percutaneous needle biopsy, ablation of a lesion (e.g. in the kidney or liver), endoscopic ultrasound (e.g. of a pancreas), or resection of an organ (e.g. a kidney or liver) to remove a lesion or tumour. In such procedures the ultrasound imaging may be performed in real time during the procedure, often in combination with video imaging. The ultrasound imaging may therefore be used to guide a surgical procedure.

However, it can be difficult to use ultrasound for guiding a surgical procedure, because the imager may not be confident of the precise position being imaged by the ultrasound, for example in relation to the lesion or tumour, and/or with regard to blood vessels (whose position may have already been identified in a pre-surgical CT or MRI scan). In such contexts a method that works rapidly (in near real-time) to register the position of an US probe would be valuable.

The issue of registration of ultrasound scan data is particularly relevant in laparoscopic procedures, in which laparoscopic ultrasound (LUS) imaging is used. LUS probes tend to have a narrow field of view, which makes registration more challenging. A relatively small section of an organ may be acquired (in contrast with transabdominal US), providing less information to constrain the registration problem.

One approach for registration of US with volumetric scan data is to track the position of the US probe, and to use this to generate a volumetric US scan, which provides more information for registration with a pre-surgical volumetric scan (e.g. from CT). Another approach is to provide a relatively accurate initial position estimate for the US probe (which may be referred to as initialisation).

A better method of registering ultrasound scan images, especially LUS scan images, to pre-existing volumetric scan data is desirable. Preferably, such a method should be simple to implement, and require minimal additional equipment.

SUMMARY

According to a first aspect of the present disclosure, there is provided a computer implemented method for identifying a pose of a probe by registering an ultrasound image from with volumetric scan data, comprising:
processing the volumetric scan data to determine simulated ultrasound images corresponding with a plurality of different poses of the probe;
extracting a feature vector from each of the simulated ultrasound images and from the ultrasound image;
comparing the feature vector from the ultrasound image with each feature vector of the simulated ultrasound images to determine a distance or similarity for each simulated ultrasound image; and
selecting at least one candidate image, the at least one candidate image comprising a subset of the simulated ultrasound images that best matches the ultrasound image, based on the distance or similarity;
identifying the pose of the probe from the at least one candidate image.

Determining a distance or similarity between each candidate image and the ultrasound image may comprise calculating a $L^2$ distance between the feature vector of the ultrasound image and the feature vector of the simulated image.

Determining a distance or similarity between each candidate image and the ultrasound image may further comprise weighting the $L^2$ distance with a term to penalise features in the feature vector of the simulated image that are not found in the feature vector of the ultrasound image.

The method may comprise identifying a probe path comprising a sequence of ultrasound images corresponding with successive poses of the probe path, wherein:
extracting a feature vector comprises extracting a feature vector from each of the simulated ultrasound images and from each of the sequence of ultrasound images;
comparing the feature vector comprises comparing the feature vector from each of the sequence of ultrasound images with each feature vector of the simulated ultrasound images to determine a distance or similarity between each of the sequence of ultrasound images and each simulated ultrasound image;
selecting at least one candidate image comprises selecting candidate simulated images that best match each of the sequence of ultrasound images; and
determining a candidate image that is most likely to match an ultrasound image comprises determining a transition probability between two candidate images.

The transition probability may be based on a kinematic model that determines a transition probability based on an expected variance in pose between successive ultrasound images of the probe path.

The probe path may be along an organ, and an expected variance in position orthogonal to a surface of the organ may be lower than an expected variance in position along the surface of the organ.

The expected variance in pose may be proportional to a time difference between successive ultrasound images of the probe path.

The transition probability between two candidate images $J_{ki}$ and $J_{ki+1}$ may be defined based on:

$$P(J_{ki+1}|J_{ki}) = \frac{\exp\left(-\frac{1}{2}\delta_{ki+1,ki}^T \sum^{-1} \delta_{ki+1,ki}\right)}{\sqrt{2\pi^4|\Sigma|}}, \Sigma = (t_{i+1} - t_i)\sum_{pose}$$

where $\delta_{ki+1,ki}$ is a vector containing differences in pose between two candidate images and $\Sigma_{pose}$ is a covariance matrix of the pose defining the expected variance of the pose parameters with respect to time.

The method may comprise imposing a transition probability penalty when a probe path direction deviates from an initial direction by more than a threshold amount.

A Viterbi algorithm may be used to determine a most probable probe path.

Selecting candidate images that best match each of the sequence of ultrasound images may comprise selecting, for each of the sequence of ultrasound images, a predetermined number of candidate images with the lowest distance or highest similarity based on the respective feature vectors.

Extracting a feature vector may comprise segmenting each of the simulated ultrasound images and the ultrasound image.

The segmentation may identify the position of blood vessels in each image, and the feature vector may comprises a position of each blood vessel and optionally a size of each blood vessel.

The feature vector may be extracted using a convolutional neural network.

The convolutional neural network may have been trained to distinguish between ultrasound images.

The pose may comprise the position of the probe on the surface of an organ, and an orientation of the probe.

The pose may further comprise a depth or deformation parameter.

The ultrasound image may be obtained by scanning a liver, kidney or pancreas.

The method may comprise displaying the pose of the probe with a 3D representation of the volumetric scan data, wherein a 3D representation of the probe pose is registered to the 3D representation of the volumetric scan data.

According to a second aspect of the invention, there is provided a non-transient machine readable medium comprising instructions for configuring a processor to perform the method of the first aspect, including any of the optional features thereof.

According to third aspect, there is provided apparatus, comprising a processor configured to perform the method according to the first aspect, including any of the optional features thereof.

The apparatus may further comprise an ultrasound probe, for acquisition of the ultrasound image or sequence of ultrasound images.

The ultrasound probe may be a laparoscopic ultrasound probe, or an endoscopic ultrasound probe.

The apparatus may further comprise a display, wherein the processor is configured to cause the display to display the pose of the probe with a 3D representation of the volumetric scan data, wherein a 3D representation of the probe pose is registered to the 3D representation of the volumetric scan data.

BRIEF DESCRIPTION OF THE DRAWINGS

Embodiments will now be described, purely by way of example, with reference to the accompanying drawings, in which.

DETAILED DESCRIPTION

Figure 1:
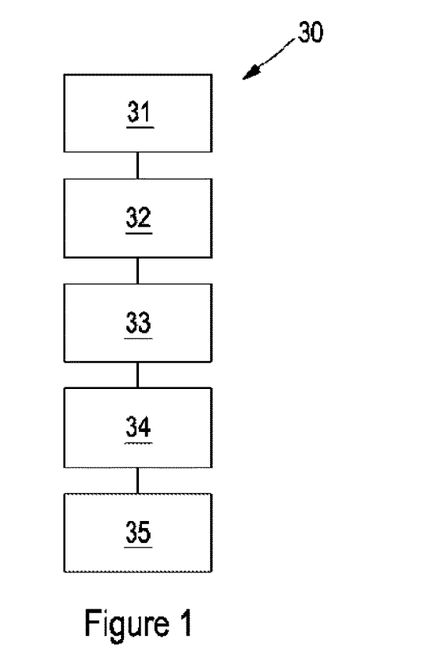
FIG. 1 is a sequence of steps according to an embodiment for determining a probe pose corresponding with an ultrasound image by registering the ultrasound image with volumetric scan data.

FIG. 1 is a sequence of steps 30 according to an embodiment of the invention, for determining a probe pose corresponding with an ultrasound image by registering the ultrasound image with volumetric scan data.

At step 31, the volumetric scan data is processed to determine a plurality of simulated ultrasound images corresponding with different poses of the probe (e.g. at least one of position, orientation, depth/deformation).

At step 32, a feature vector is extracted from each of the simulated ultrasound images, and from the ultrasound image. The feature vector may comprise a position and size of each vessel intersection with the respective image. The feature vector may be obtained by segmentation of the images into vessels and not-vessels.

At step 33, the feature vector from each simulated ultrasound image is compared with the feature vector from the ultrasound image to determine a distance or similarity value.

At step 34, a candidate image is selected as the best match, based on the distance or similarity.

At step 35, the pose of the probe is identified from the candidate image.

Figure 2:
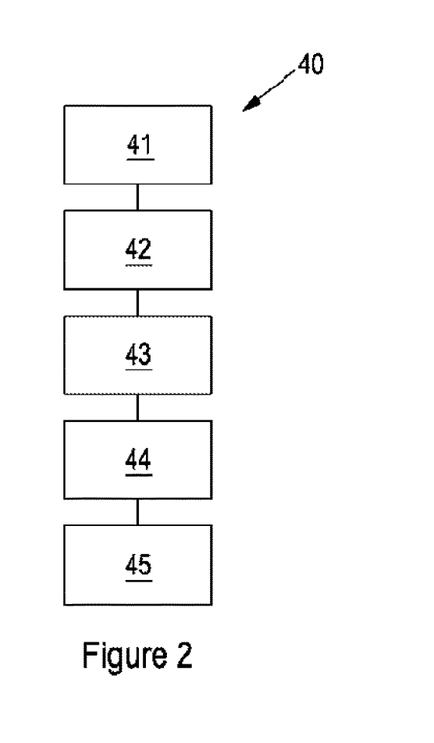
FIG. 2 is a sequence of steps according to an embodiment for determining a sequence of probe poses corresponding with a sequence of ultrasound images by registering the sequence of ultrasound images with volumetric scan data.

FIG. 2 illustrates a sequence of steps 40, according to an embodiment of the invention, for determining a sequence of probe poses corresponding with a sequence of ultrasound images obtained by sweeping the probe over tissue, such as an organ, by registering the sequence of ultrasound images with volumetric scan data.

At step 41, the volumetric scan data is processed to determine a plurality of simulated ultrasound images corresponding with different poses of the probe (e.g. at least one of position, orientation, depth/deformation).

At step 42, a feature vector is extracted from each of the simulated ultrasound images, and from each of the sequence of ultrasound images. The feature vector may comprise a position and size of each vessel intersection with the respective image. The feature vector may be obtained by segmentation of the images into vessels and not-vessels.

At step 43, the feature vector from each simulated ultrasound image is compared with the feature vector from each of the sequence of ultrasound images to determine a distance or similarity value.

At step 44, candidate simulated images are selected that best match each of the sequence of ultrasound images, based on the distance or similarity.

At step 45, a probe path is identified by determining from the candidate images which is most likely to match each ultrasound image in the sequence of ultrasound images using a transition probability between two candidate images. The transition probability may be based on kinematic assumptions about the movement of the probe over time. A hidden Markov model may be used to determine the simulated images that are most likely to correspond with the sequence of ultrasound images.

Figure 3:
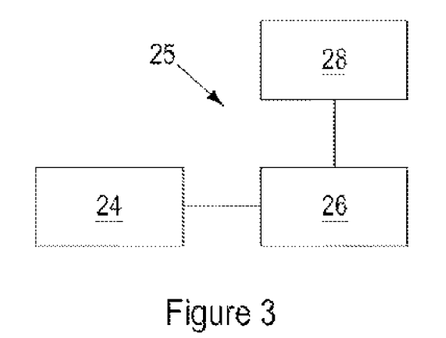
FIG. 3 is an example apparatus according to an embodiment.

FIG. 3 shows apparatus 25, comprising an ultrasound probe 24, processor 26 and display 28. The ultrasound probe 24 may be a laparoscopic ultrasound probe that is configured to obtain ultrasound data for generating an ultrasound image of an organ during a laparoscopic surgical procedure. The processor 26 may be configured to receive the ultrasound data from the probe 24, and determine an ultrasound image therefrom. The processor 26 may further comprise a memory that includes volumetric scan data. The processor 26 may be configured to determine a probe pose corresponding with an ultrasound image by registering the ultrasound image with the volumetric scan data, for example in accordance with method steps 30 or 40. The processor 26 may further be configured to cause the display to display the pose of the probe (or the sweep, comprising probe poses) with a 3D representation of the volumetric scan data, wherein a 3D representation of the probe pose(s) is registered to the 3D representation of the volumetric scan data.

Example embodiments will be described in more detail with reference to FIGS. 4 to 13

Given a set of N, 2D ultrasound images $\{I_1, \ldots, I_N\}$ and corresponding acquisition time stamps $\{t_i, \ldots, t_N\}$, embodiments of the invention can recover the sequence of US images, simulated from pre-operative volumetric scan data (e.g. obtained by CT) $\{J_1, \ldots, J_N\}$ that most closely represent the US acquisition in terms of features defined in a feature vector. Conveniently, the feature vector may be based on vascular content. Content based image retrieval may be used to obtain a set of K possible images $\{J_{i1}, \ldots, J_{Ki}\}$ as candidates for each image $I_i$, based on a comparison of a feature vector of the image $I_i$ with each of the simulated US images $\{J_1, \ldots, J_N\}$. In one embodiment, the set of K possible images is the a single US image with a feature vector that is most similar to the ultrasound image $I_i$. In other embodiments, a Viterbi algorithm may be applied with kinematic prior information in order to find the most likely sequence of simulated US images $\{J_1, \ldots, J_N\}$ and hence the corresponding pose of the probe in each of a sequence of US images $\{I_1, \ldots, I_N\}$.

The set of simulated US images J may be obtained by intersecting a segmented model of the volumetric scan data with 2D planes, bounded by an LUS field of view. The model of the volumetric scan data may be segmented to indicate "blood vessel" and "not blood vessel". A set of evenly distributed points $P_S$ may be generated over the surface of the organ of interest (e.g. liver). At each of these points $P_S$ a virtual reference orientation may be created, orthogonal to the organ surface normal and with the imaging plane aligned with the sagittal plane. At each point $P_S$, different combinations of rotations $R_x$, $R_y$, and $R_z$ may be applied to generate simulated US images corresponding with rotated projections parameterised by $R=[\vec{x}, \vec{y}, \vec{z}]$. In addition, at each point $P_S$, a number of translations d may be applied along the organ surface normal, simulating the case in which the probe compresses the tissue of the organ and images deeper structures. For each combination of $P_S$, R and d, a binary image containing vessel sections may be generated.

Figure 4:
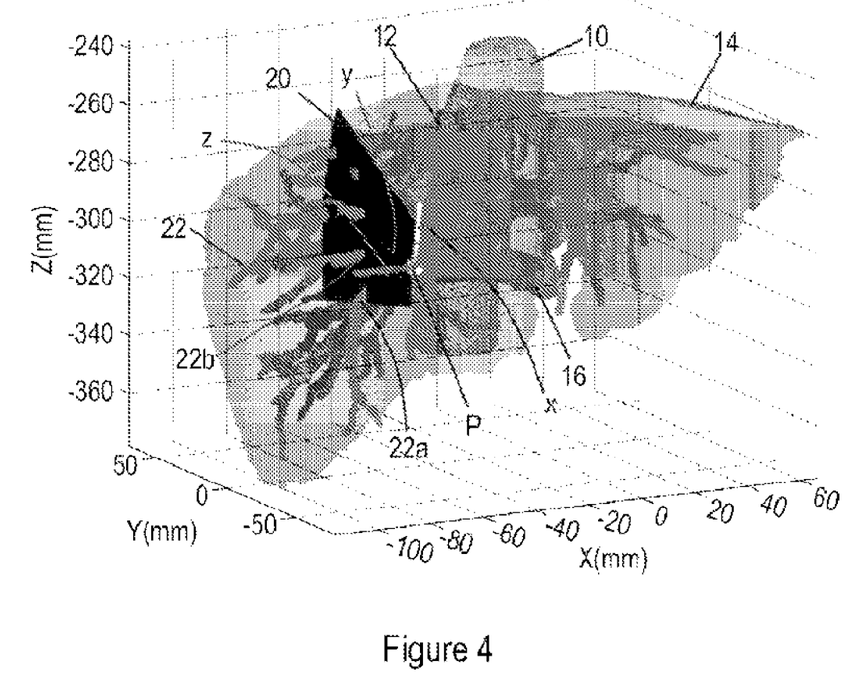
FIG. 4 is a 3D model of liver with blood vessels and the inferior vena cava, obtained from a CT scan, with a laparoscopic ultrasound probe field of view for a particular probe location.

FIG. 4 illustrates the generation of an example simulated US image from CT scan data. A model of the liver 14 is obtained from the CT scan data along with a model of the inferior vena cava 10. The blood vessels 22 of the liver 14, including the hepatic vein 12 and portal vein 16, are also modelled. The simulated probe position P is shown, with probe body co-ordinates x, y and z. The field of view of the simulated scan 20 is indicated, which intersects with a number of blood vessels 22a, 22b etc.

Figure 5:
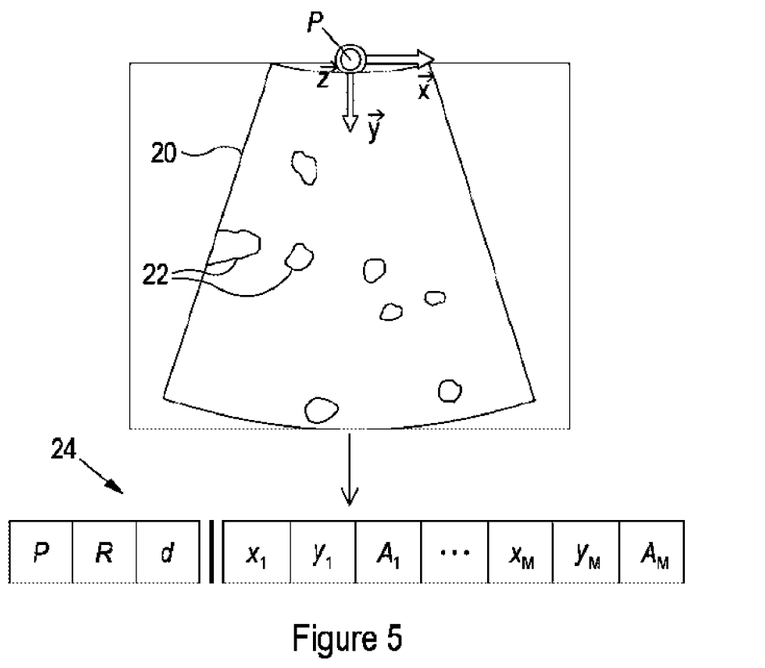
FIG. 5 is a an ultrasound scan simulated using CT scan data that is binarised to show blood vessels in white and not blood vessels in black, and including a feature vector extracted from the simulated ultrasound scan.

FIG. 5 shows an example simulated ultrasound image 20, comprising black regions that are not vessels, and white regions 22 that are vessels. In this example image there are 8 separate (non-contiguous) vessel regions, in various positions. The vessel information content of the simulated ultrasound image 20 may be captured in a feature vector $f$. In one embodiment, the centroid (with respect to the probe co-ordinates x and y) and the area of each vessel may be encoded in a feature triplet $f_i$. The triplets may be concatenated with the pose of the probe (comprising the position P, rotation R and translation d), to form the feature vector $f$ as illustrated in FIG. 5.

Other approaches may be used to produce a feature vector. For example, principle component analysis may be used to compress the simulated images to produce a feature vector, or the first n layers of a convolutional neural network that has been trained to discriminate between different ultrasound images may be used to produce a feature vector.

In order to compare an ultrasound image with each simulated ultrasound image, a corresponding feature vector must be extracted from the ultrasound image. For embodiments where the feature vector encodes the position and area of vessels intersecting the imaging plane, the ultrasound image must be segmented to identify the vessels, to produce a feature vector that can be compared with the feature vectors obtained from each simulated ultrasound image. The ultrasound image may be automatically segmented, for example using a convolutional neural network (e.g. as described in reference 10).

Feasible candidate poses for an input ultrasound image I may be obtained by comparing its feature vector $f^1$ to all the pre-computed vectors $f$, obtained by from the volumetric scan data, for example by calculating a weighted $L^2$ distance:

$$D(f^S, M^S, f^L, M^L) = \left( \frac{\sum_1^{M^L} A(f_i^L)}{\sum_1^{M^S} A(m(f_i^S, f^L))} \right) \cdot \sum_{i=1}^{M^S} \|f_i^S - m(f_i^S, f^L)\|^2 \quad (1)$$

where $f^S$ is a feature vector with a smaller number of vessel sections $M^S$, and $f^L$ is a feature vector with a larger number of vessel sections $M^L$. In equation (1), the function $m(f_i^S, f^L)$ returns the feature triplet values in $f^L$ with the closest lumen centroid to that of triplet $f_i^S$ and the function $A(\cdot)$ returns the area value from a triplet. An area ratio is used to penalise the exclusion of triplet from the longer vector $f^L$: the total area of all vessels in $f^L$ is divided by the sum of the ones that were included in the matching. The larger the excluded areas, the larger D becomes, and therefore the less similar the feature vectors.

To perform an efficient search, it is possible (but not essential) to only search for feature vectors that have a similar number of triplets (corresponding with vessel sections) to the input $f^1$. Feature vectors may be grouped in lookup tables $F_M$ according to their size M. The search for the best candidates $f^*$ may as expressed in equation (2):

$$f^* = \underset{f^T \in F_T}{\operatorname{argmin}} \frac{D(f^1, M^1, f^T, M^T)}{\min(M^1, M^T)}, \quad F_T = \bigcup_{l=-r}^{r} F_{M_l+l} \quad (2)$$

Here, the distance D is computed between $f^1$ and members of the lookup tables of size $M^1-r$ to $M^1+r$, where r is the allowable limit of the feature vector length differences. The results may be normalised by the minimum number of sections used in each comparison, and a lowest set of K candidate $f^*$ vectors picked. These vectors become a set of CT images $\{J_{1i}, \ldots, J_{Ki}\}$ with corresponding probe poses.

Once a set of k possible matches $\{J_{1i}, \ldots, J_{Ki}\}$ are obtained for image $I_i$ a transition probability may be used to determine a set of simulated images from J that match the set of acquired images $\{I_1, \ldots, I_N\}$ acquired by sweeping the probe over the surface of the organ. Under these conditions, each successive acquired image will correspond with a successive pose along the path swept by the probe as it moves over the surface of the organ. This imposes a kinematic constraint on the set of images selected from J to match the acquired images $\{I_1, \ldots, I_N\}$ because solutions that require very high acceleration and/or velocity are very unlikely to be correct.

Figure 6:
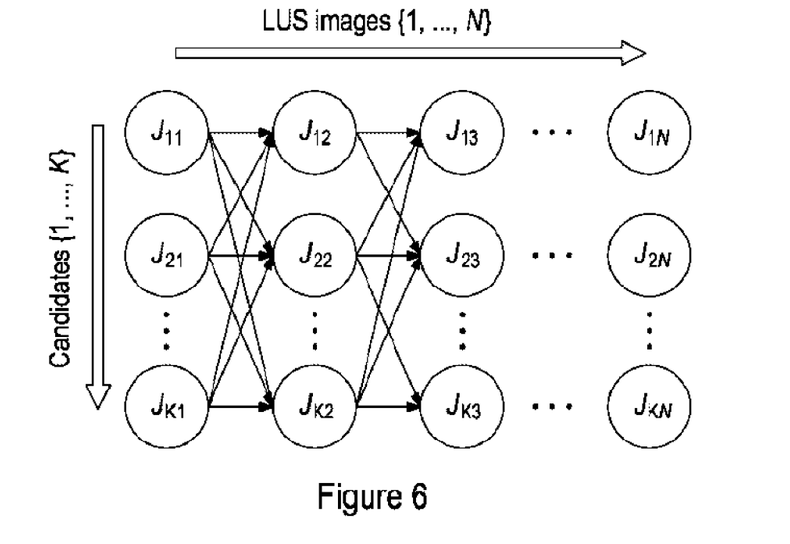
FIG. 6 is a hidden Markov model of the problem of mapping a set of ultrasound scan images to a set of candidate simulated ultrasonic images corresponding with known probe locations in a volumetric scan (such as a CT scan)
Figure 7:
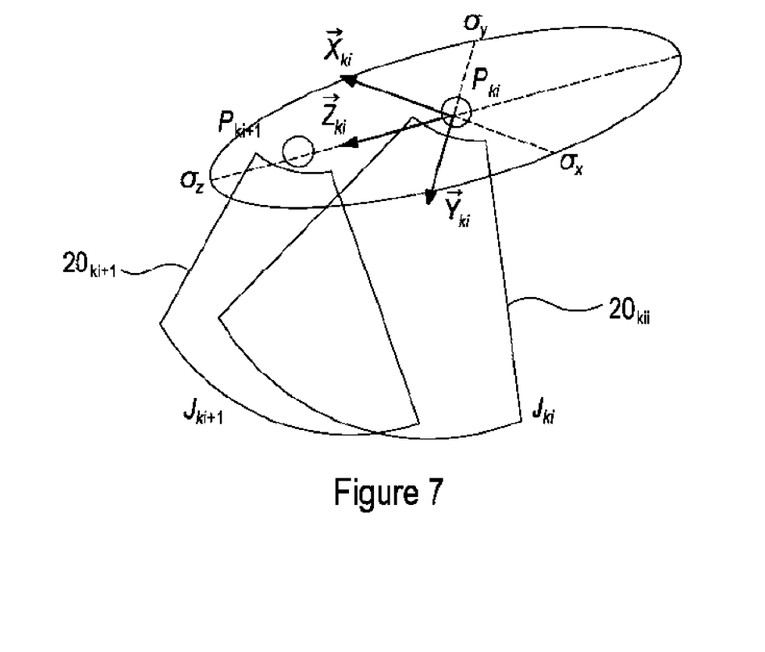
FIG. 7 is a visual representation of a translation probability density function of an image $J_{ki}$ being followed by image $J_{ki+1}$.

This can be formulated as a hidden Markov model, as shown in FIG. 6. Nodes in FIG. 6 represent a probability of each acquired image $I_i$ matching a candidate simulated image $J_{ki}$, and edges represent a probability associated with an input kinematic prior. The kinematic prior may be selected to constrain the selected images to match a condition of the kinematics of the acquisition. For example, it may be assumed that there is smoothness in the acquisition, and/or it may be assumed that the probe follows a continuous path along a direction normal to the imaging plane without moving backwards. Neither of these are essential, and the prior assumptions may be altered for acquisitions with different kinematics. In addition to constraints such as these, a transition probability may be defined between two candidate simulated images (selected from J), based on the following Gaussian:

$$P(J_{ki+1}|J_{ki}) = \frac{\exp\left(-\frac{1}{2}\delta_{ki+1,ki}^T \Sigma^{-1} \delta_{ki+1ki}\right)}{\sqrt{2\pi^4|\Sigma|}}, \quad \Sigma = (t_{i+1} - t_i)\begin{bmatrix} \Sigma_t & 0 \\ 0 & \sigma_\theta \end{bmatrix} \quad (3)$$

where $\delta_{ki+1,ki}$ is a vector containing the differences in rotation and translation between the two candidates. As shown in FIG. 7, this is the 3D difference between probe contact points $P_{ki+1}$ and $P_{ki}$, projected along the orientation $R_{ki}$ of $J_{ki}$, and the angle between the imaging plane normals $\vec{z}_{ki+1}$ and $\vec{z}_{ki}$. The covariance matrix $\Sigma$ is expressed in block matrix notation and holds a variance $\sigma_\theta$ and a diagonal translation covariance $\Sigma_t$ with three terms $\sigma_x$, $\sigma_y$ and $\sigma_z$. Equation (3) models a Gaussian probability distribution centred on the pose of the previous image $J_{ki}$, with variance proportion to the time difference between the current image $J_{ki+1}$ and the previous image $J_{ki}$. The lower the time difference, the lower the pose difference should be.

Other expressions may be used to model the transition probability—it is not essential to assume that the probability distribution is Gaussian, for example.

The values for $\sigma_x$, $\sigma_y$ and $\sigma_z$ may be selected based on knowledge of the speed that the probe is expect to move during the acquisition sweep. It is likely that the speed of movement in the z direction, normal to the plane of the imaging scan (as shown in FIG. 7) will be larger than the speed in either x or y, so $\sigma_z$ may be defined to be larger than both $\sigma_x$ and $\sigma_y$, thereby favouring movement along the surface of the organ along the image plane normal.

One way to find the optimal sequence of candidates is to use the Viterbi algorithm to find the lower cost path. In some embodiments, each of the candidate simulated images corresponding with the vector $f^*$ of best matches may be assumed to be equally likely to match the current acquired image, and the node probabilities $P(I_i|J_{ki})$ assumed to be 1 (leaving it to the kinematic transition probability to determine the best matching set of images). In other embodiments, the node probabilities $P(I_i|J_{ki})$ may be weighted by the distance D (e.g. according to equation (1), in addition to the kinematic prior).

During optimisation, a constraint may be implemented to reject candidate simulated image sets that do not fulfil specific kinematic conditions. For example, a sweep direction may be defined as the difference between the first two probe positions $P_{k2}-P_{k1}$ in the candidate simulated image set. The probability $P(I_i|J_{ki})$ may be set to 0 (or reduced by a predetermined amount or ratio) if the angle between $P_{ki+i}-P_{ki}$ and the sweep direction is above 90 degrees (or some other predetermined angle or variance).

EXAMPLES

A method according to an embodiment was applied to acquired ultrasonic data from three patients. Pre-operative models of the liver and vasculature were segmented (following a similar approach to reference 4), and respective databases of simulated images and feature vectors generated using rotation angles in the intervals $R_x=R_z=[-40°, 40°]$, $R_y=[-90°, 90°]$ with steps of 10° and depth values in the interval d=[0,20 mm] with steps of 5 mm. The spatial resolution between successive positions P was [3-4 mm]. The probability $P(I_i|J_{ki})=1$, and a hard constraint was implemented, setting the probability $P(I_i|J_{ki})$ to zero in the event the angle between $P_{ki+1}-P_{ki}$ and $P_{k2}-P_{k1}$ is greater than 90 degrees.

Initially, the validity of this approach was tested by registering synthetic sweeps generated from a CT model to itself. For each of the three patients, three smooth trajectories were generated, comprising 20 images with time stamps t=[1, . . . , 20s]. Retrieval with search limit r=0 was used to find K=200 candidates for each ultrasound image, and registrations were performed using variances $\sigma_z=1.5$ mm, $\sigma_x$.32 $\sigma_y=0.2\sigma y$ and $\sigma_\theta=2$.

Figure 8:
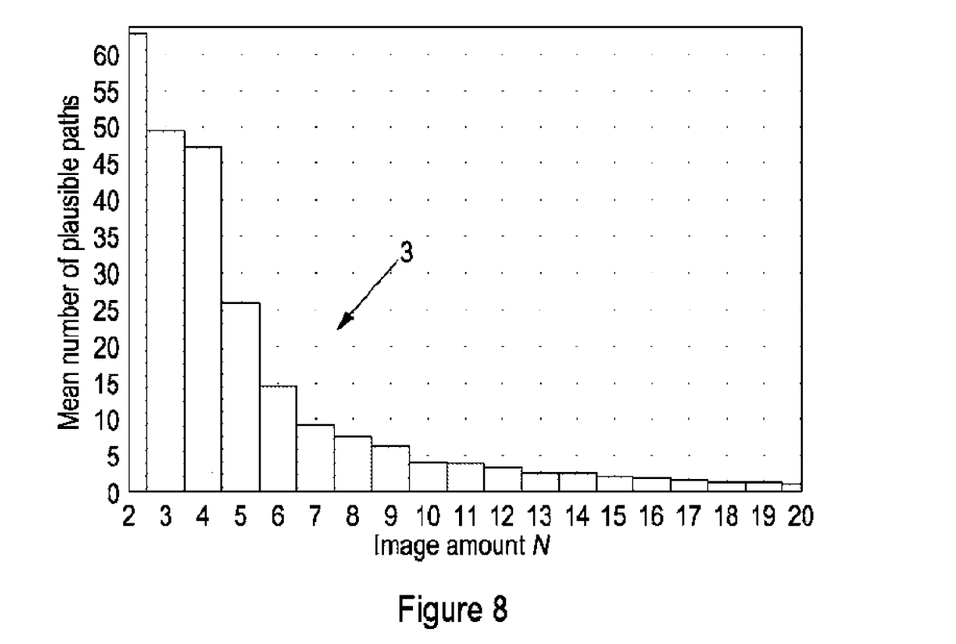
FIG. 8 is a graph showing the mean number of plausible paths mapping a set of ultrasound images obtained from a scan of an ultrasound probe against the number of images in the set.

The mean number of plausible paths 2 for each of the nine sweep registrations vs the number of images is shown in FIG. 8. Since the Viterbi algorithm is recursive on the number of columns in the hidden Markov model (shown in FIG. 6), results are displayed as a function of the number of images used so far in the optimisation (from 2 to 20). FIG. 8 therefore shows the number of kinematically possible paths for N images (i.e. with a non-zero probability, based on the constraints defined above). The number of plausible trajectories found by the algorithm converges to 1 if enough images are used (N=17 in this case).

Figure 9:
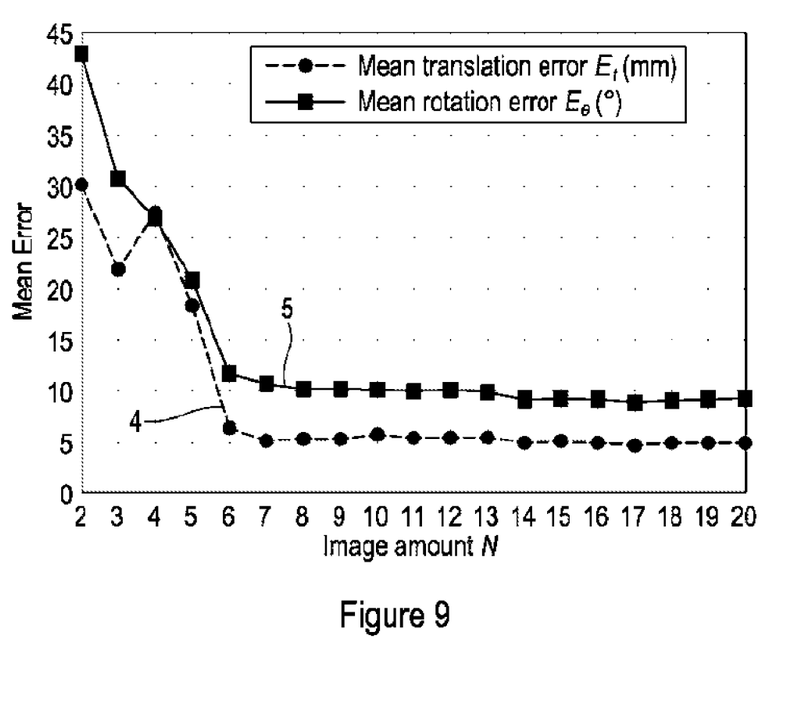
FIG. 9 is a graph showing translation and rotation error of the registrations obtained from the optimal path.
Figure 10:
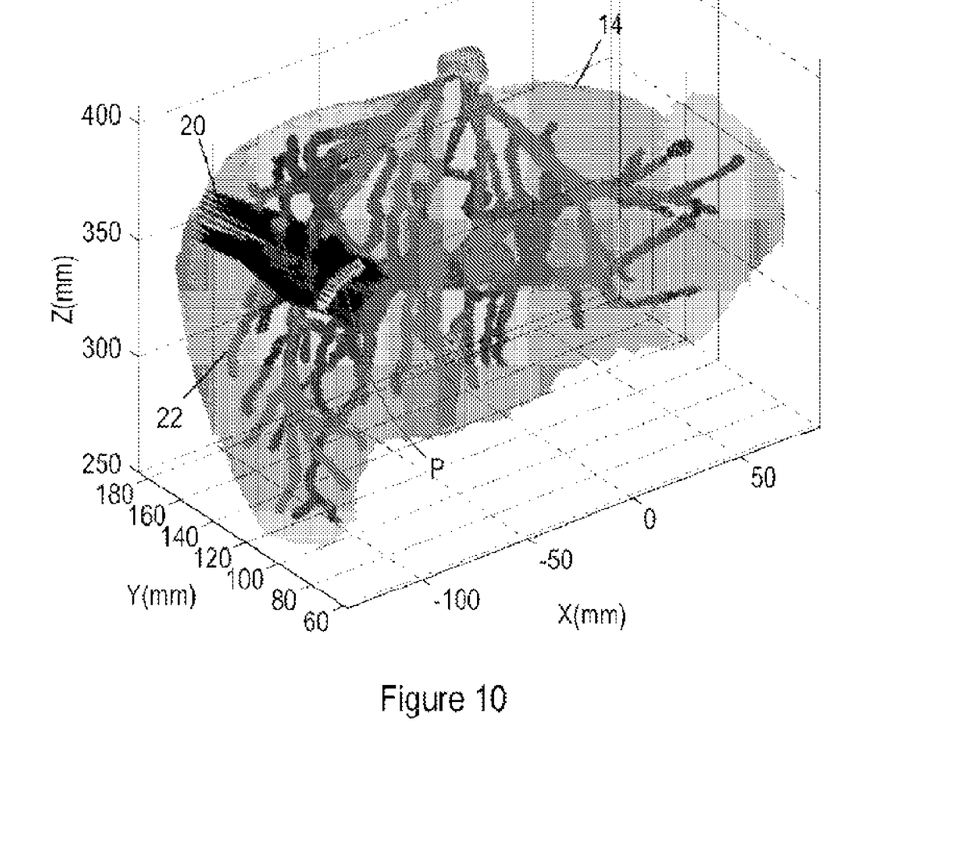
FIG. 10 is a ground truth probe path of an ultrasound sweep shown in the context of a model of the liver from a CT scan.

FIG. 9 shows the mean translation error $E_t$ 4 and mean rotation error $E_\theta$ 5 across all N registered images for the lowest cost path. Here the convergence may be observed in terms of error: at an average number of 7 images, the error converges to 5 mm and 10°. The rotation resolution of the CT model is 10° and the liver surfaces used have a spatial resolution in the range [3-4 mm], so the converged values are as accurate as can realistically be achieved for this synthetic test case.

To demonstrate the utility of embodiments on real data, LUS scans acquired intra-operatively were retrospectively registered with CT scan data. The LUS probe was a BK Medical 8666-RF probe, operating at a frame rate of 40 Hz. From each patient, two sequences of contiguous images were selected, and segmented to identify vessels and non-vessels. Manual segmentation was used to demonstrate the methodology, but automatic segmentation may also be used (as already mentioned above).

A search was performed to find k=1000, with r=2. The translation variance values were doubled over those defined above, with $\sigma_z$=3 mm, $\sigma_x$=$\sigma_y$=0.2$\sigma_y$, and $\sigma_\theta$=2°. For each sweep, LUS images were manually registered to CT data to provide a ground truth trajectory. After obtaining a solution, the errors $E_t$ and $E_\theta$ were measured, and a Target Registration Error (TRE) determined of a set of manually picked vessel bifurcations found in the path. Since these bifurcations may land in images in between the sequence that were not registered, a cubic polynomial fit was used to predict their position given the algorithm solution.

Table 1 shows the results from the six sweeps.

TABLE 1

N is the number of images in the sweep. $N_C$ the number of images the Viterbi algorithm requires to converge in error. $E_t$ and $E_\theta$ are the mean translation and rotation error respectively. TRE is the Root Mean Square (RMS) error of the manually picked landmarks found in the sweep.

|  | Patient 1 | | Patient 2 | | Patient 3 | |
| --- | --- | --- | --- | --- | --- | --- |
| Dataset | Sweep 1 | Sweep 2 | Sweep 1 | Sweep 2 | Sweep 1 | Sweep 2 |
| N | 42 | 12 | 25 | 11 | 23 | 19 |
| $N_C$ | 6 | 8 | 16 | 6 | 19 | 16 |
| $E_t$ (mm) | 14.7 | 18.7 | 11.2 | 10.3 | 19.1 | 15.3 |
| $E_\theta$ (°) | 14.8 | 33.3 | 17.2 | 13.9 | 44.1 | 32.3 |
| TRE (mm) | 18.8 | 3.7 | 14.2 | 11.4 | 25.3 | 21.9 |

Figure 11:
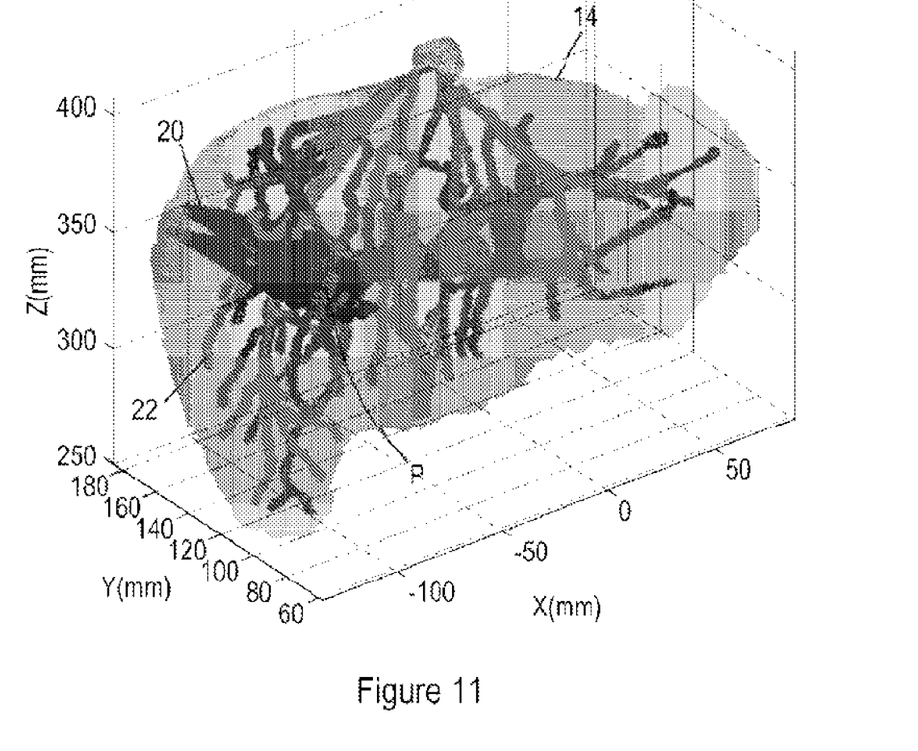
FIG. 11 shows the path obtained in accordance with an embodiment of the present disclosure, shown in the context of the liver from the CT scan, for comparison with FIG. 10.

The best trajectory registration results are found in the sweeps of patient 2, with translation errors of around 10 mm. A visual display of the result of sweep 2 from patient 2 is shown in FIG. 11, which may be compared with the ground truth trajectory shown in FIG. 10. The agreement between ground truth and the probe positions obtained is good.

Figure 12:
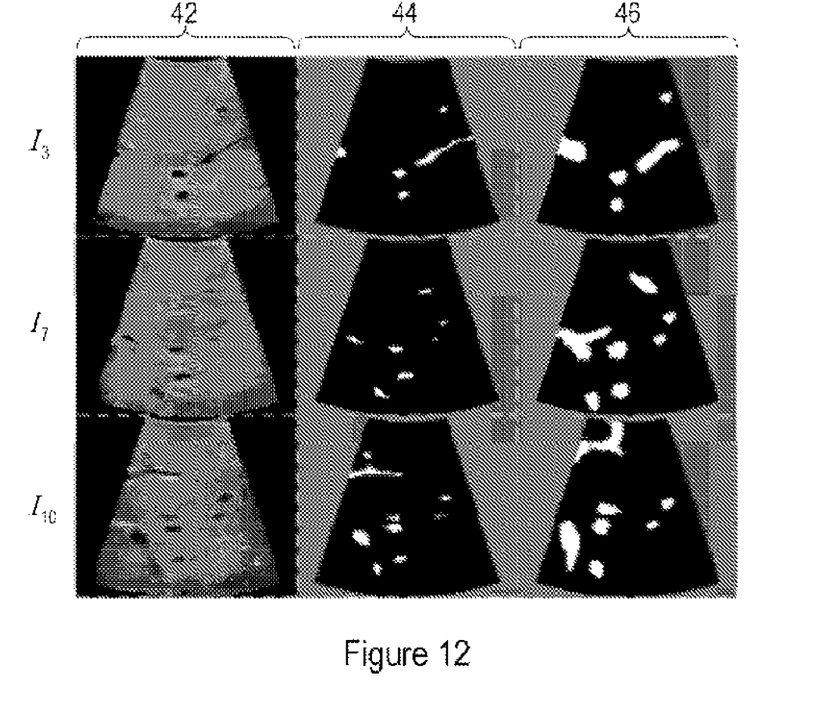
FIG. 12 compares ultrasound, segmented ultrasound and simulated CT alignment images for three locations in the sweep illustrated in FIG. 11.

FIG. 12 shows a comparison between the ultrasound images 42, the segmented ultrasound images 44 and the simulated images 46 selected as the best match, for image $I_3$, $I_7$ and $I_{10}$.

Figure 13:
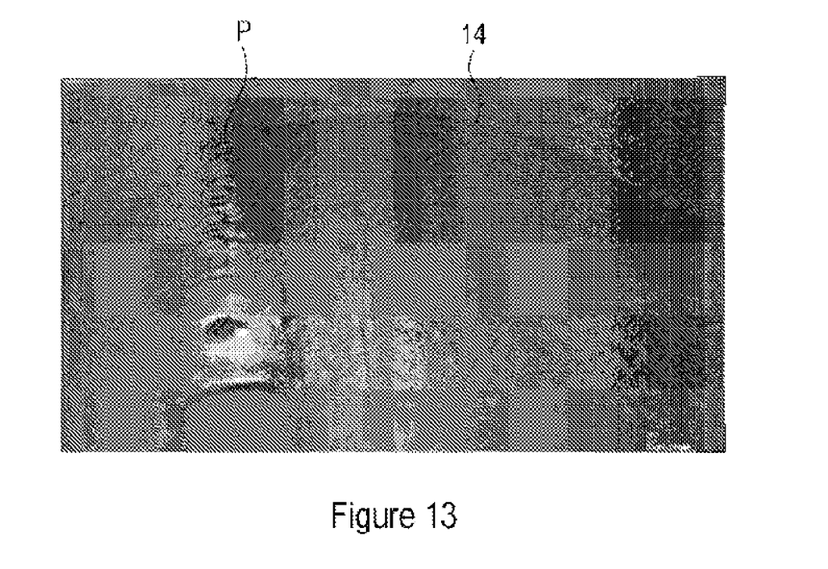
FIG. 13 is an image of a laparoscopic ultrasound probe acquiring an ultrasound image from a liver.

FIG. 13 shows a video image of a laparoscopic ultrasound probe in position P on the surface of the liver 14, taken during the procedure.

The best trajectory registration results are found in the sweeps of patient 2, with translation errors around 10 mm. Lowest accuracies are obtained for patient 3, but these do not surpass 20 mm. This value is still usable as this is a globally optimal alignment (on the whole liver).

The number of images $N_C$ at which the errors converge varies greatly, which may be due to the variation in uniqueness of registered images that is specific to each patient dataset. The TRE results are in the range of [3.7-25.3 mm] and are therefore in reasonable agreement with the other errors.

The results show that embodiments can register smaller field of view images (e.g. from an LUS probe) to a larger volume (e.g. an organ larger than the field of view of the LUS probe) globally and without tracking information. Embodiments may provide for a reduction in manual interaction and less interruption to clinical work flow, since a tracking device is not required.

In the example described herein, it is implicit that the organ does not deform. In some embodiments, the set of simulated ultrasound images obtained from the volumetric scan may be parameterised to include deformation (e.g. in the y direction). In some embodiments the depth d parameter may represent deformation of the organ in a direction normal to the surface of the organ (rather than a simple translation without deformation). Higher accuracies may be achievable with parameterisation including deformation.

Although specific embodiments have been described variations are possible within the scope of the invention. The scope of the invention should be determined with reference to the accompanying claims.

REFERENCES

1. Wakabayashi, G., Cherqui, D., Geller, D. A., Buell, J. F., Kaneko, H., et al.: Recommendations for laparoscopic liver resection: a report from the second international consensus conference held in Morioka. Ann. Surg. 261(4), 619{629 (2015)
2. Wein, W., Brunke, S., Khamene, A., Callstrom, M. R., Navab, N.: Automatic CTultrasound registration for diagnostic imaging and image-guided intervention. Med. Image. Anal. 12(5), 577{585 (2008)
3. Penney, G. P., Blackall, J. M., Hamady, M. S., Sabharwal, T., Adam, A., Hawkes, D. J.: Registration of freehand 3D ultrasound and magnetic resonance liver images. Med. Image. Anal. 8(1), 81{91 (2004)
4. Song, Y., Totz, J., Thompson, S., Johnsen, S., Barratt, D., et al.: Locally rigid, vessel-based registration for laparoscopic liver surgery. IJCARS pp. 1{11 (2015)
5. Ramalhinho, J., Robu, M., Thompson, S., Edwards, P., Schneider, C., et al.: Breathing motion compensated registration of laparoscopic liver ultrasound to CT. In: Proc. SPIE Medical Imaging (2017)
6. Ramalhinho, J., Robu, M. R., Thompson, S., Gurusamy, K., Davidson, B., et al.: A pre-operative planning framework for global registration of laparoscopic ultrasound to CT images. IJCARS 13(8), 1177{1186 (2018)
7. Petrakis, E. G. M., Faloutsos, A.: Similarity searching in medical image databases IEEE Trans Knowl Data Eng 9(3), 435{1447 (1997)
8. Cifor, A., Risser, L., Heinrich, M. P., Chung, D., Schnabel, J. A.: Rigid registration of untracked freehand 2D ultrasound sweeps to 3D CT of liver tumours. In: Yoshida, H., War eld, S., Vannier, M. W. (eds.) Abdominal Imaging. Computation and Clinical Applications. pp. 155{164. Springer Berlin Heidelberg, Berlin, Heidelberg (2013)

9. Nir, Guy, et al. "Registration of whole-mount histology and volumetric imaging of the prostate using particle filtering." IEEE transactions on medical imaging 33.8 (2014): 1601-1613.
10. Smistad, Erik, and Lasse Løystakken. "Vessel detection in ultrasound images using deep convolutional neural networks." Deep Learning and Data Labeling for Medical Applications. Springer, Cham, 2016. 30-38.
11. Brudfors, Mikael, et al. "Towards real-time, tracker-less 3D ultrasound guidance for spine anaesthesia." International journal of computer assisted radiology and surgery 10.6 (2015): 855-865.
12. Wein, Wolfgang, et al. "Automatic bone detection and soft tissue aware ultrasound—CT registration for computer-aided orthopedic surgery." International journal of computer assisted radiology and surgery 10.6 (2015): 971-979.

What is claimed is:

1. A computer implemented method for identifying a pose of a probe by registering an ultrasound image with volumetric scan data, comprising:
  processing the volumetric scan data to determine simulated ultrasound images corresponding with a plurality of different poses of the probe;
  extracting a feature vector from each of the simulated ultrasound images and from the ultrasound image;
  comparing the feature vector from the ultrasound image with each feature vector of the simulated ultrasound images to determine a distance or similarity for each of the simulated ultrasound images;
  selecting at least one candidate image, the at least one candidate image comprising a subset of the simulated ultrasound images that best matches the ultrasound image, based on the distance or similarity;
  identifying the pose of the probe from the at least one candidate image; and
  wherein the volumetric scan data is pre-operative volumetric scan data.

2. The method of claim 1, wherein determining a distance or similarity between each of the simulated ultrasound images and the ultrasound image comprises calculating a $L^2$ distance between the feature vector of the ultrasound image and the feature vector of the simulated ultrasound image.

3. The method of claim 2, wherein determining a distance or similarity between each of the simulated ultrasound images and the ultrasound image further comprises weighting the $L^2$ distance with a term to penalise features in the feature vector of the simulated ultrasound image that are not found in the feature vector of the ultrasound image.

4. The method of claim 1, wherein the method comprises identifying a probe path comprising a sequence of ultrasound images corresponding with successive poses of the probe path, wherein:
  extracting a feature vector comprises extracting a feature vector from each of the simulated ultrasound images and from each of the sequence of ultrasound images;
  comparing the feature vector comprises comparing the feature vector from each of the sequence of ultrasound images with each feature vector of the simulated ultrasound images to determine a distance or similarity between each of the sequence of ultrasound images and each of the simulated ultrasound images;
  selecting at least one candidate image comprises selecting candidate simulated images that best match each of the sequence of ultrasound images; and
  determining a candidate image that is most likely to match the ultrasound image comprises determining a transition probability between two candidate images.

5. The method of claim 4, wherein the transition probability is based on a kinematic model that determines the transition probability based on an expected variance in the pose between successive ultrasound images of the probe path.

6. The method of claim 5, wherein the probe path is along an organ and an expected variance in position orthogonal to a surface of the organ is lower than an expected variance in position along the surface of the organ, or wherein the expected variance in pose is proportional to a time difference between successive ultrasound images of the probe path, or comprising imposing a transition probability penalty when a probe path direction deviates from an initial direction by more than a threshold amount.

7. The method of claim 4, wherein the transition probability between two candidate images $J_{ki}$ and $J_{ki+1}$ is defined based on:

$$P(J_{ki+1}|J_{ki}) = \frac{\exp\left(-\frac{1}{2}\delta_{ki+1,ki}^T \Sigma^{-1} \delta_{ki+1,ki}\right)}{\sqrt{2\pi^4|\Sigma|}}, \Sigma = (t_{i+1} - t_i)\Sigma_{pose}$$

where $\delta_{ki+1,\ ki}$ is a vector containing differences in the pose between the two candidate images and $\Sigma_{pose}$ is a covariance matrix of the pose defining the expected variance of parameters of the pose with respect to time.

8. The method of claim 4, wherein a Viterbi algorithm is used to determine a most probable probe path, or wherein selecting the at least one candidate images that best match each of the sequence of ultrasound images comprises selecting, for each of the sequence of ultrasound images, a predetermined number of candidate images with the lowest distance or highest similarity based on the respective feature vectors.

9. The method of claim 1, wherein extracting the feature vector comprises segmenting each of the simulated ultrasound images and the ultrasound image.

10. The method of claim 9, wherein the segmentation identifies a position of blood vessels, and the feature vector comprises the position of each blood vessel and a size of each blood vessel.

11. The method of claim 1, wherein the feature vector is extracted using a convolutional neural network.

12. The method of claim 11, wherein the convolutional neural network has been trained to distinguish between ultrasound images.

13. The method of claim 1, wherein the pose comprises the position of the probe on the surface of an organ, and/or an orientation of the probe.

14. The method of claim 13, wherein the pose further comprises a depth or deformation parameter.

15. The method of claim 1, wherein the ultrasound image is obtained by scanning a liver, kidney or pancreas, or comprising displaying the pose of the probe with a 3D representation of the volumetric scan data, wherein a 3D representation of the probe pose is registered to the 3D representation of the volumetric scan data.

16. A non-volatile machine readable medium comprising instructions for configuring a processor to perform operations for identifying a pose of a probe by registering an ultrasound image with volumetric scan data, said operations comprising:

processing the volumetric scan data to determine simulated ultrasound images corresponding with a plurality of different poses of the probe;

extracting a feature vector from each of the simulated ultrasound images and from the ultrasound image;

comparing the feature vector from the ultrasound image with each feature vector of the simulated ultrasound images to determine a distance or similarity for each of the simulated ultrasound images;

selecting at least one candidate image, the at least one candidate image comprising a subset of the simulated ultrasound images that best matches the ultrasound image, based on the distance or similarity; and identifying the pose of the probe from the at least one candidate image.

17. The apparatus of claim 16, further comprising an ultrasound probe, for acquisition of the ultrasound image or sequence of ultrasound images.

18. The apparatus of claim 17, wherein the ultrasound probe is a laparoscopic ultrasound probe or an endoscopic ultrasound probe.

19. The apparatus according to claim 16, further comprising a display, wherein the processor is configured to cause the display to display the pose of the probe with a 3D representation of the volumetric scan data, wherein a 3D representation of the probe pose is registered to the 3D representation of the volumetric scan data.

20. A computer system comprising one or more non-transitory computer readable memories which store, in combination or singularly, instructions that, when executed by a one or more computers, cause the one or more computers to perform operations for identifying a pose of a probe by registering an ultrasound image with volumetric scan data, said operations comprising:

processing the volumetric scan data to determine simulated ultrasound images corresponding with a plurality of different poses of the probe;

extracting a feature vector from each of the simulated ultrasound images and from the ultrasound image;

comparing the feature vector from the ultrasound image with each feature vector of the simulated ultrasound images to determine a distance or similarity for each of the simulated ultrasound images;

selecting at least one candidate image, the at least one candidate image comprising a subset of the simulated ultrasound images that best matches the ultrasound image, based on the distance or similarity; and identifying the pose of the probe from the at least one candidate image.

\* \* \* \* \*